United States Patent [19]

Cobia et al.

[11] Patent Number: Plant 7,174

[45] Date of Patent: Feb. 27, 1990

[54] PLANT OF THE CACTACEAE PLANT FAMILY 'SANTA CRUZ'

[75] Inventors: Barnell L. Cobia, Winter Garden; Mark E. Cobia, Orlando, both of Fla.

[73] Assignee: B. L. Cobia, Inc., Winter Garden, Fla.

[21] Appl. No.: 283,988

[22] Filed: Dec. 12, 1988

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Roger L. Martin

[57] ABSTRACT

A new and distinct plant variety of the Cactaceae family is of the type known commercially as a "Christmas Cactus" and has a growth habit which is similar to that the "Twilight Tangerine" variety (U.S. Plant Pat. No. 4,200) but which, nevertheless, differs, among other things, by having phylloclades with longer and thicker midribs and thicker wings and teeth, a bloom with more intense salmon coloration, and flowers which are sterile and have a sepaloid series of tepals with a smaller number of tepals and shorter tepal lengths and smaller tepal widths, a tube laminating series of tepals with a larger number of tepals and greater tepal widths, a tube forming series of tepals with greater widths, and a longer perianth tube.

4 Drawing Sheets

BACKGROUND OF THE INVENTION

The invention relates to a new and distinct plant variety of the Cactaceae family and which has been named the *Zygocactus truncatus* 'Santa Cruz' by the inventors.

Certain plant varieties of the Cactaceae family are well known in the foliage plant market and among these are those which are commonly referred to as the Christmas Cactus varieties because they tend to bloom during the Thanksgiving-Christmas holiday season in the northern hemisphere.

The Christmas Cactus varieties on the market have blooms which vary in color from one variety to the next as is evident from the current U.S. patent art. One of the more popular varieties sold commercially in the market place is the variety that has been named *Zygocactus truncatus* 'Twilight Tangerine'. This variety has a bloom that is salmon color and it represents an improvement on one of its predecessor varieties known as "Christmas Cheer". "Twilight Tangerine" forms the subject matter of U.S. Plant Pat. No. 4,200 and the relationship between it and "Christmas Cheer" is set forth therein.

SUMMARY OF THE INVENTION

A general objective has been to develop a new plant variety with a bloom color which, in comparison to the bloom color exhibited by the "Christmas Cheer" and patented "Twilight Tangerine" varieties, is more intense in that there is a greater dominance of the reddish orange hue in the bloom coloration, and wherein the new plant variety is capable of being marketed in competition with the older varieties.

The objective has been fully realized by the development of the new plant variety hereinafter described in detail. The new plant variety was developed in a nursery located in Winter Garden, Fla., from a mutation that appeared on a specimen of an unmarketed research variety (ZH18227) and which was under cultivation at the nursery. The research variety and the "Twilight Tangerine" variety have a common heritage and are second generation descendants of yet another variety.

The new plant variety has a more erect posture than its source research variety (ZH18227). In addition, it has phylloclades with thicker wings, midribs and teeth, and a bloom with wider tepals and a color which is more pronouncely influenced by a reddish orange hue.

Through successive propagations of cuttings taken from the mutated plant part, it has been ascertained that specimens of the new plant variety generally resemble the "Twilight Tangerine" variety in most respects but are distinguishable from this variety and from other related varieties known to the inventors by a growth habit which is evident in plant specimens of the new variety that have been propagated and grown under nursery conditions utilized in the growing of tropical plants in Winter Garden, Fla., as combining the following principal characteristics:

1. A more erect posture at maturity than the "Twilight Tangerine" variety.

2. Phylloclades which, in comparison to the "Twilight Tangerine" variety, have (a) longer and thicker midribs, (b) thicker wings, and (c) thicker teeth, 3. Flowers which, in comparison to the "Twilight Tangerine" variety, are sterile and have (a) a bloom with a greater dominance of a reddish orange hue in the coloration, (b) a sepaloid tepal series with a smaller number of tepals and which have a shorter length and smaller width, (c) a tube laminating tepal series with a larger number of tepals and which have a greater width, (d) a tube forming tepal series with tepals that have a greater width, (e) a longer perianth tube, (f) an androecium with a smaller number of tube attached stamens, and both the tube attached and basally united stamens having filaments that are longer and with greater diameters, and (g) a gynoecium with a style that is longer and and has a larger diameter and ovaries that are shorter in length and have a smaller number of carpules, the ovaries having longer major and minor axes at the distal ends of the concavities.

BRIEF DESCRIPTION OF THE DRAWINGS

The accompanaying drawings serve by color photographic means to illustrate the new plant variety and wherein one sheet show a nine (9) month old specimen which was grown from the propagation of a single phylloclade in a conventional 3 in. pot found in the marketplace. A second sheet shows an enlargement of a fully open bloom taken from the specimen shown in the first mentioned sheet. Still another sheet shows the fully open bloom illustrated in the second sheet together with a bloom as sectioned generally longitudinally through the perianth tube and ovary to expose the style and stamen arrangement. The last sheet show four plant parts that include phyllocades taken from a specimen of the new variety, each plant part having one or more attached buds or blooms to illustrate the flowers in progressive stages of maturity.

DETAILED PLANT DESCRIPTION

The following is a detailed description of the new plant variety with colors and hues, unless otherwise clearly indicated by the text, as, for example, through the absence of color notations, being used in accord with the ISCC-NBS Method of Designating Colors (U.S. Dept. of Commerce, National Bureau of Standards, Circular 553), the named colors being interpreted from color notations derived by comparison with color specimens of the Munsell Book of Color. The description is further based on observations of well fertilized plants about one year old from initial propagation and which are grown under 50–75% shaded glasshouse nursery conditions in the Winter Garden, Fla. area and wherein temperatures range from 60°–85° F. during the winter months, from 75°–95° F. during the summer months, and are ambient during athe intervening periods.

I. Name: *Zygocactus truncatus* 'Santa Cruz'.

II. Parentage: This variety was developed from a mutation that occurred on a specimen of an unmarketed research variety (ZH18227) which shares a ancestry which is in part common to that of the variety known as "Twilight Tangerine" and which in turn forms the subject matter of U.S. Plant Pat. No. 4,200.

III. Classification:

A. *Botanic* (*Britton and Rose, The Cactaceae,* Constable and Co., Ltd., London 1937, vol. IV).—(1) Family: Cactaceae. (2) Tribe: Cereeae. (3) Sub-Tribe: Epiphyllanae. (4) Genus: Zygocactus. (5) Species: *Truncatus* (Haworth) Schumann.

B. *Commercial.*—Thanksgiving–Christmas blooming cactus.

IV. Form: Epiphylic and terrestrial shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pitch surrounding vascular bundles that branch and provide lateral extensions of the vascular system to the marginal teeth. (b) Texture — Smooth, waxy epidermis with wax in small embedded scales and becoming woody in basal stem areas with specimen ageing. (c) Size (at maturity) — 1. Length: Usually 27–63 mm. 2. Thickness: Usually 3.5–7.5 mm. (d) Color (at maturity) — Usually dominated by a olive green hue. Commonly moderate yellow green (5 GY 5/6) (7.5 GY 5/6) (7.5 GY 4/6) and/or moderate olive green (7.5 GY 4/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with speicmen aging. (d) Size (at maturity) — 1. Thickness: About 2–4 mm in the area intermediate the margin and midrib. 2. Width: Usually 12–19 mm as measured from phylloclade axis to most offset lateral areole. (e) Color (at maturity) — Usually dominated by an olive green hue. Commonly moderate olive green (7.5 GY $\frac{3}{4}$) (7.5 GY 4/6) (7.5 GY 4/4). (4) Teeth: (a) Shape — 1. General: Generally flattened and tapering along the margins from the insertion in the wing to an apex that has a hyaline, single cell, pointed spine with non-predictable bending. 2. Abaxial margin: Usually straight to convex. 3. Adaxial margin: Usually straight to concave. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1–2 mm in center area. 2. Areole to apex dimension (adaxial marginal side): Usually 2.5–14 mm. (f) Number — Usually 6–9 per phylloclade. (g) Color — Usually dominated by an olive green hue. Commonly moderate olive green (7.5 GY $\frac{3}{4}$) (7.5 GY 4/4). (5) Areoles: (a) Terminal areole — Large, elongated, oval shaped with several acicular bristles, and several buds that may mature into either new phylloclades or flowers. The opposite ends of the areole are located adjacent to subsidiary areoles which are, in turn, located at the axils of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid tepal series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 3–5. (5) Size (at full bloom): (a) Length (base-tip dimension) — Usually less than 11 mm. (b) Width (maximum) — Usually less than 9 mm. (6) Color (at full bloom): Varies from the outer members to the inner members with the smallest outer whorl tepals usually having a continuous field that in color is dominated by a yellow green hue. The inner whorl tepal members have marginal and center blade areas that in color are dominated by a reddish orange and/or yellowish pink hue that projects into a translucent white basal area. Commonly strong reddish orange (7.5 R 5/12), moderate reddish orange (7.5 R 6/10) and/or strong yellowish pink (7.5 R 7/8) in marginal and center blade ageas of the inner whorl members and moderate yellow green (2.5 GY 7/6) and/or strong yellow green (2.5 GY 7/8) (2.5 GY 6/8) in the basal areas of outer whorl members. (7) Orientation: Erect to recurve at full bloom.

C. *Tube laminating tepal series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the the whorl from ovate with an acute tip to spatulate with a broader acute tip. Margins entire to fimbriolate or erose with sparse, irregular teeth mainly in apex areas. (3) Texture: Succulent and glabrous outer whorl members and grading inwardly to silken blades with slightly fleshy basal areas. (4) Number: Usually 7–9 tepals. (5) Size (at full bloom): (a) Length (base-tip dimension) — Usually ranging from about 13 to about 54 mm. (b) Width (maximum) — Usually ranging from about 10 to about 21 mm. (6) Color (at full bloom): (a) General — Tepals with basal areas that are white in color and/or in color are dominated by a yellow green hue immediately above the insertion, and with marginal and center blade areas that in color are dominated by a reddish orange hue which extends proximally to merge with the distally extending basal area color. (b) Basal area — Commonly brilliant yellow green (5 GY 8/8) and/or light yellow green (2.5 GY 9/6) (5 GY 9/6) in the outer whorl members and transluscent white in the inner whorl members. (c) Blade area — Commonly strong reddish orange (7.5 R 5/12) and/or moderate reddish orange (7.5 R 6/10) in marginal and center blade areas. (7) Orientation: Perpendicular to recurve at full bloom.

D. *Tube forming tepal series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with acute tips and entire margins that become finbriolate or erose with sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 7–10. (5) Size (at full bloom): (a) Perianth tube — 1. Length (base-keel): Usually 25–36 mm along tube axis. 2. Major Axis: Usually 10–12 mm at throat interior. 3. Minor axis: Usually 6–9 mm at throat interior. (b) Blades — 1. Length (keel-tip): Usually 29–36 mm. 2. Width (maximum): Usually 14–20 mm. (6) Color (at full bloom): (a) Perianth tube — A basic field that is translucent white with longitudinally extending, randomly arranged striations or streaks that, in color, are dominated by a yellowish pink hue. Commonly strong yellowish pink (7.5 R 7/8). (b) Blades — A continuous marginal and center blade area that is nearly uniform in color distally of the keel, the color being usually dominate by a reddish orange and/or yellowish pink hue. Commonly translucent white in the area proximate to the keel and moderate reddish orange (7.5 R 6/10), strong yellowish pink (7.5 R 7/8) and/or strong reddish orange (7.5 R 5/12) in the marginal and center blade areas. (c) Carina (keel) — Color usually dominated by a purplish pink and/or purplish red hue. Commonly moderate purplish red (5 RP 5/10) and/or deep purplish pink (5 RP 6/10). (7) Orientation: Acute to recurve and/or revolute.

E. *Androecium (stamens).*—(1) General: Numberous exserted and diadelphous stamens with one group having filaments basally fused to the perianth tube and the other group having filaments basally united to form a nectary housing, thin annulus around the style and which is provided with a thin, deflexed, irregular, toothed margin or ruffle at the throat of the annulus. (2) Stamen number: (a) Tube attached group — Usually 43–63. (b) Basally united group—Usually 16–20. (3) Filaments: (a) General — Translucent with anther connective. (b) Shape — Long, slender, terete. (c) Texture — Glabrous and capillaceous. (d) Color — Usually translucent white over entire length. (e) Size (at full bloom) — 1. Length: a. Tube attached group — Usually 37–56 mm. b. Basally united group — Usually 35–51 mm. 2. Diameter: Usually about 0.5 mm at insertion and tapering to about 0.25 mm at distal end. (4) Anthers: (a) General — Adnate with four longitudinally dehiscent pollen sacs and connective inserted at end. (b) Shape — Elongated. (c) Texture — Waxy. (d) Color (before dehiscence) — Dominated by a yellow hue. Commonly pale yellow (5 Y 9/4) and/or light yellow (5 Y 9/6). (e) Sterility — Sterile.

F. *Gynoecium* (*pistil*).—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish purple hue and progressively varying in color between basal and distal ends. Commonly strong reddish purple (2.5 RP 5/10) and/or light reddish purple (2.5 RP 6/8) at basal end and strong reddish purple (2.5 RP 4/10) at the distal end. (e) Size (at full bloom) — 1. Length: Usually 52–60 mm. 2. Diameter: Usually 1.0–1.5 mm intermediate opposite ends. (3) Stigma: (a) General — Exserted and erect with usually 5–8 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a reddish purple hue. Commonly light reddish purple (2.5 RP 6/8) and/or strong reddish purple (2.5 RP 5/10). (e) Size — 1. Length: Usually 5–7 mm along inner margins. (4) Ovary: (a) General — Inferior with thin epidermis and usually 5–6 carpules with numerous ovules. (b) Shape — Terete to avoid and generally broadening from insertion to floral end. Ribbed single concavity with inserted style. (c) Texture — Succulent with glabrous thin outer epidermis. (d) Color — A basic field with color usually dominated by a yellow green hue. Commonly moderate yellow green (5 GY 5/6) (2.5 GY 5/6) and/or strong yellow green (2.5 GY 6/8). (e) Size — 1. Length: Usually 5–8 mm from insertion to cavity base. 2. Major axis: Usually 9–11 mm at distal end of concavity. 3. Minor axis: Usually about 8–10 mm at distal end of concavity.

VIII. Growth habit: Erect.

General Description of a Plant Specimen

Age of plant: Nine (8) months from initial propagation of single phylloclade.

Branches from propagated phylloclade: Three (3).

Total number of new phylloclades grown: Twelve (12).

GENERAL:

| Branch No. | No. of Phylloclades | Maximum Branch Length | No. of Tips |
|---|---|---|---|
| 1 | 4 | 158 mm | 1 |
| 2 | 4 | 178 mm | 1 |
| 3 | 4 | 179 mm | 1 |

MIDRIBS:

| Branch No. | Average Midrib Length | Average Midrib Thickness |
|---|---|---|
| 1 | 39.5 mm | 5.0 mm |
| 2 | 44.5 mm | 4.8 mm |
| 3 | 44.8 mm | 4.3 mm |

WINGS:

| Branch No. | Average Wing Center Thickness | Average Wing Width (Maximum) |
|---|---|---|
| 1 | 2.5 mm | 16.0 mm |
| 2 | 2.8 mm | 15.8 mm |
| 3 | 2.4 mm | 16.0 mm |

TEETH:

| Branch No. | Teeth (Avg.) per Phylloclade | Avg. Tooth Center Thickness | Avg. Aerole to Apex Length |
|---|---|---|---|
| 1 | 7.25 | 1.4 mm | 5.3 mm |
| 2 | 8.5 | 1.6 mm | 6.0 mm |
| 3 | 8.5 | 1.6 mm | 5.3 mm |

Phylloclade color: Moderate yellow green (5 GY 5/6) and moderate olive green (7.5 GY 3/4) (7.5 GY 4/6) (7.5 GY 4/4).

General Description of a Flower

The following is a general description of a flower of the new plant variety and which bloomed in December on an 8 month old plant specimen grown under shaded greenhouse nursery conditions in Winter Garden, Fla., U.S.A.

No. of buds and blooms on plant specimen: 7.

Bloom life: 8 days.

Sepaloid tepal series:

*Number.*—5.

*Tepal size* (*at full bloom*).—Maximum base-tip dimension: 10 mm. Minimum base-tip dimension: 5 mm. Maximum width dimension: 8 mm.

*Color* (*at full bloom*).—Strong yellow green (2.5 GY 7/8) and moderate yellow green (2.5 GY 7/6) in the continuous field of the small outer whorl tepal members. Strong reddish orange (7.5 R 5/12) and strong yellowish pink (7.5 R 7/8) in the marginal and center blade areas and transluscent white, moderate yellow green (2.5 GY 7/6) and strong yellow Green (2.5 GY 7/8) in the basal areas of the inner whorl members.

Tube laminating tepal series:

*Number.*—9.

*Size* (*at full bloom*).—Maximum base-tip dimension: 52 mm. Minimum base-tip dimension: 13 mm. Maximum blade width: 19 mm. Minimum blade width: 12 mm.

*Color.*—Strong reddish orange (7.5 R 5/12) and moderate reddish orange (7.5 R 6/10) in the marginal and center blade areas and translucent white to light yellow green (2.5 GY 9/6) (5 GY 9/6) in the basal areas of the blades.

Tube forming tepal series:

*Number.*—9.

*Size* (*at full bloom*).—Periant tube: Length (base to keel) — 33 mm along tube axis. Major axis — 12 mm at throat interior. Minor axis — 8 mm at throat interior. Blades: Maximum length (keel-tip) — 34 mm. Minimum length (keel-tip) — 33 mm. Maximum blade width — 19 mm. Minimum blade width — 16 mm.

*Color.*—Perianth tube: A basic field that is generally transluscent white with random striations of strong yellowish pink (7.5 R 7/8). Blades: Transluscent white in basal area proximate to keel and moderate reddish orange (7.5 R 6/10), strong yellowish pink (7.5 R 7/8) and/or strong reddish orange (7.5 R 5/12) in marginal and center field areas.

Androecium:

*Stamen number.*—Tube attached group: 60. Basally united group: 19.

*Filaments.*—Color: translucent white. Size: Length — Tube attached group: 49 mm (avg.). Basally united group: 45 mm (avg.). Diameter — About 0.35 mm intermediate the opposite ends.

*Anthers.*—Color (before dehiscing): Light yellow (5 Y 9/6).

Gynoecium (pistil):

*Style.*—Color: Strong reddish purple (2.5 RP 5/10) and light reddish purple (2.5 RP 6/8) in basal area and strong reddish purple (2.5 RP 4/10) in the distal area. Size (at full bloom): Length — 57 mm. Diameter — 1.0 mm intermediate opposite ends.

*Stigma.*—Color: light reddish purple (2.5 RP 6/8) and strong reddish purple (2.5 RP 5/10). Size: 6 mm (avg.) lobe length.

*Ovary.*—Color: Moderate yellow green (2.5 GY 5/6) and strong yellow green (2.5 GY 6/8). Size (at full bloom): Length (insertion to concavity base) — 8 mm. Major axis — 10 mm at distal end of concavity. Minor axis — 9 mm at distal end of concavity.

We claim:

1. A new and distinct plant variety of the Cactaceae family as shown and described and which is mainly distinguished from its antecedents and known related varieties by a growth habit which is similar to that of the "Twilight Tangerine" variety but as modified by the combination of the characteristics which follow:

(1) A more erect posture at maturity than the "Twilight Tangerine" variety.

(2) Phylloclades which, in comparison to the "Twilight Tangerine" variety, have (a) longer and thicker midribs, (b) thicker wings, and (c) thicker teeth, (3) Flowers which, in comparison to the "Twilight Tangerine" variety, are sterile and have (a) a bloom with a greater dominance of a reddish orange hue in the coloration, (b) a sepaloid tepal series with a smaller number of tepals and which have a shorter length and smaller width, (c) a tube laminating tepal series with a larger number of tepals and which have a greater width, (d) a tube forming tepal series with tepals that have a greater width, (e) a longer perianth tube, (f) an androecium with a smaller number of tube attached stamens, and both the tube attached and basally united stamens having filaments that are longer and with greater diameters, and (g) a gynoecium with a style that is longer and and has a larger diameter and ovaries that are shorter in length and have a smaller number of carpules, the ovaries having longer major and minor axes at the distal ends of the concavities.

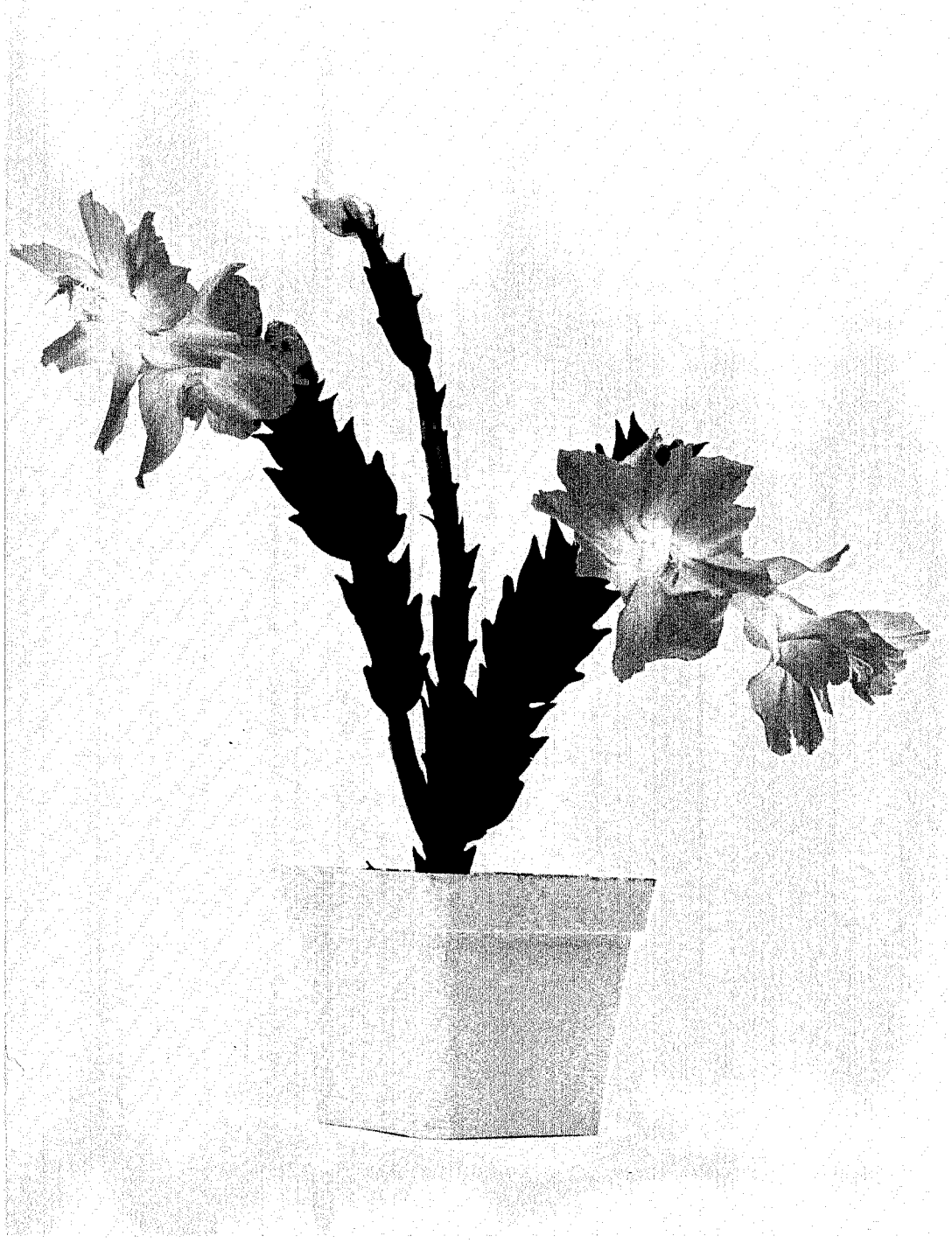

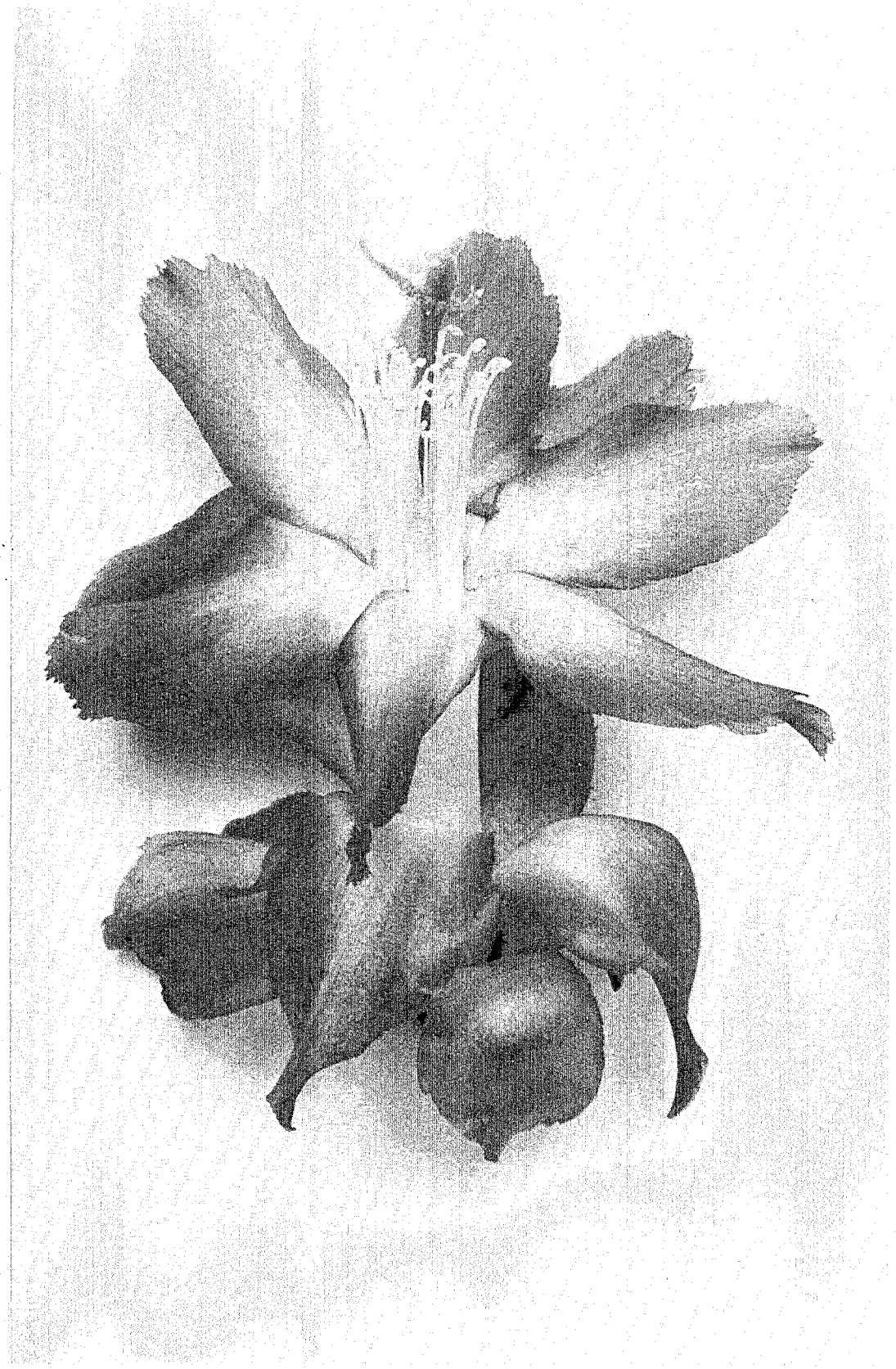

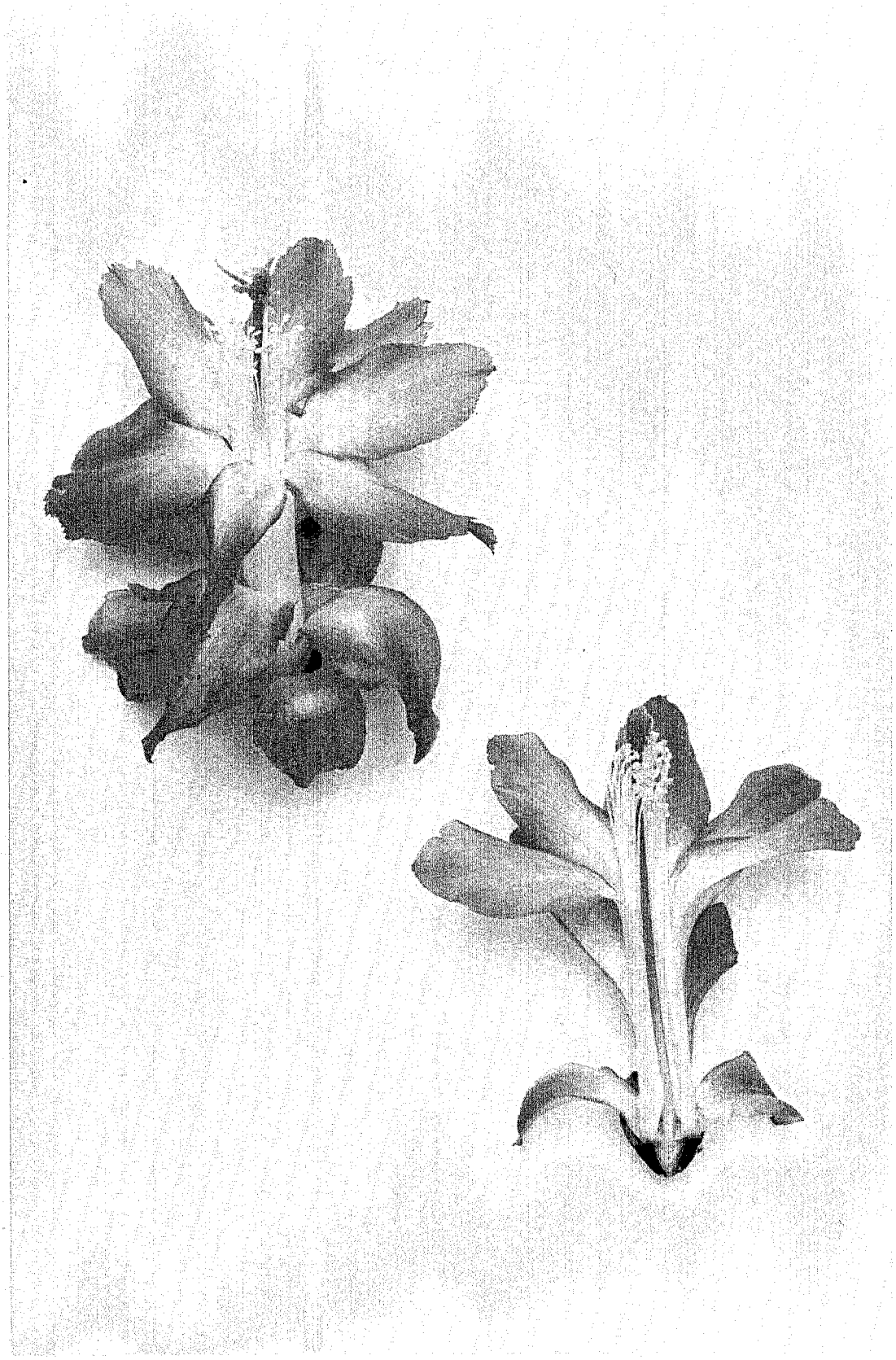

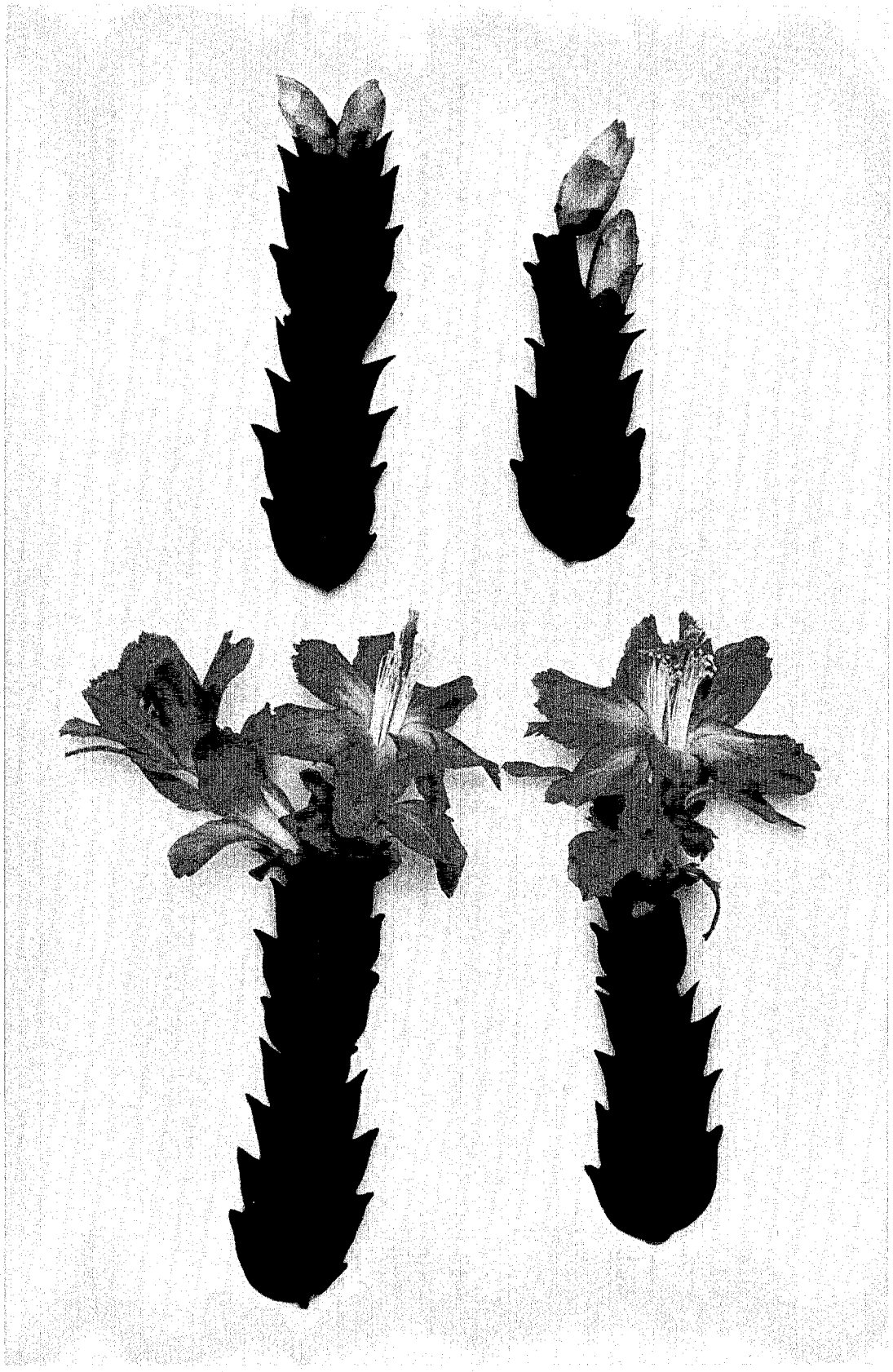

* * * * *